United States Patent
Meneguzzo et al.

(10) Patent No.: US 6,492,514 B1
(45) Date of Patent: Dec. 10, 2002

(54) BIFUNCTIONAL PHOTOINITIATORS SUITABLE FOR PHOTOPOLYMERIZATION AND PHOTOPOLYMERIZABLE SYSTEMS CONTAINING THE SAME

(75) Inventors: Enzo Meneguzzo, Sesto Calende (IT); Marco Visconti, Varese (IT); Domenico Badone-Italy, Induno Olona (IT); Giuseppe Li Bassi, Gavirate (IT)

(73) Assignee: Lamberti S.p.A., Albizzate (IT)

( * ) Notice: Subject to any disclaimer, the term of this patent is extended or adjusted under 35 U.S.C. 154(b) by 0 days.

(21) Appl. No.: 09/856,260

(22) PCT Filed: Nov. 5, 1999

(86) PCT No.: PCT/EP99/08497

§ 371 (c)(1),
(2), (4) Date: May 16, 2001

(87) PCT Pub. No.: WO00/31030

PCT Pub. Date: Jun. 2, 2000

(30) Foreign Application Priority Data

Nov. 19, 1998 (IT) .......................................... MI98A2508

(51) Int. Cl.$^7$ ...................... C07C 317/06; C07D 265/30
(52) U.S. Cl. ...................... 544/158; 544/107; 544/161; 568/29; 568/31
(58) Field of Search ................................ 544/107, 158, 544/161; 568/29, 31

(56) References Cited

FOREIGN PATENT DOCUMENTS

CS           276057     *  3/1992

OTHER PUBLICATIONS

STN International ®CAPLUS Database, Accession No. 1990:235927; Lukac, et al. J. Polym. Sci., Part A: Polym. Chem. (1990), 28(3), 595–608, Abstract.*

* cited by examiner

*Primary Examiner*—Ceila Chang
*Assistant Examiner*—Sonya Wright
(74) *Attorney, Agent, or Firm*—Abelman, Frayne & Schwab

(57) ABSTRACT

The present invention relates to compounds of general formula (I)

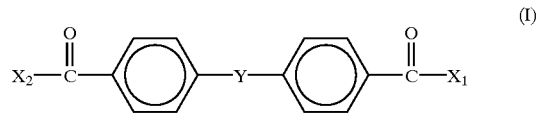

wherein $X_1$ and $X_2$ are different form each other and have the meanings reported in the following description Y is a simple bond, $C_1$–$C_{12}$ linear or branched alkyl groups, —O—, —S—, >S=O, >SO$_2$, NR$_{17}$—, wherein R$_{17}$ is H, $C_1$–$C_{12}$ linear or branched alkyl groups, COR$_1$, and photopolymerisable formulations containing as photoinitiators the aforementioned compounds of formula (I).

6 Claims, No Drawings

BIFUNCTIONAL PHOTOINITIATORS SUITABLE FOR PHOTOPOLYMERIZATION AND PHOTOPOLYMERIZABLE SYSTEMS CONTAINING THE SAME

This application is a 371 of PCT/EP99/08497 filed Nov. 5, 1999.

FIELD OF INVENTION

The present invention concerns new compounds containing in the same molecule two functional groups, which can give rise to radicals by a photochemical process. The compounds are suitable as polymerisation photoinitiators in photopolymerisable formulations containing ethylenic unsaturated systems.

PRIOR ART

Known photoinitiators contain in the molecule a functional group, which can give rise to radicals by excitation by an electromagnetic radiation, generally an UV radiation. These compounds are reported, for instance, in U.S. Pat. No. 3,715,293, DE 2722264, EP 161463, EP 3002, EP 88050, EP 284561, EP 192967, EP 850253. They are commonly used in polymerisation of ethylenic unsaturated systems. When pigmented systems are involved, such as in printing inks, the irradiating light cannot fully penetrate into the layer due to reflection and absorption of the pigment in the formulation. To obtain a good polymerization degree both at the surface level and in the inner layers of an ink, i.e. the so called surface and through cure of an ink, it is common practice to prepare formulations containing both a photoinitiator with a maximum UV absorption in the region of 250 nm and a photoinitiator with a significant absorption in the region above 300 nm. In fact above 300 nm most pigments have minimum in absorption and reflection (optical window) allowing the penetration of the light. The combination of the two kind of photoinitiators allows both surface and through cure of the formulation.

SUMMARY OF THE INVENTION

We have now surprisingly discovered the subject of the present invention, namely that molecules containing in their structure two different active moieties, both suitable to give rise to radicals, display high activity as photoinitiators, in particular in pigmented systems. The molecules can develop surprising synergies in comparison with the combined use of two photoinitiators containing each only one of the corresponding photoactive groups.

Moreover the absence in the molecule of functional groups that release volatile, odorous products by photolysis, improves the safety in the working environment, limiting the presence of volatile substances during the photopolymerisation stages in industrial processes.

Molecules generally used for the above mentioned purposes are based on two phenyl groups linked together, each substituted by a photochemically active ketonic moiety. The aromatic groups can be further substituted by non-photochemically active moieties. Among these molecules those based on two phenyl rings connected together through a suitable linking group and substituted in positions 4,4' by two ketonic moieties are the most suitable.

Therefore the present invention deals with compounds having formula (I)

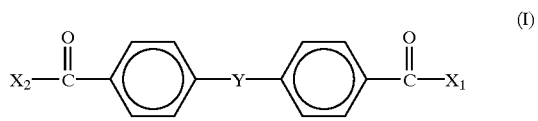

wherein $X_1$ and $X_2$ are different $X_1$ is a group

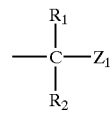

wherein $R_1$ and $R_2$, each independently, are —H or $C_1$–$C_{12}$ linear or branched or cyclic alkyl chain, aryl, alkylaryl groups.

$Z_1$ is —$SO_2R_3$, —$NR_4R_5$, —$OR_1$, halogen.

$R_3$ is: $C_1$–$C_{12}$ linear or branched alkyl chain, or:

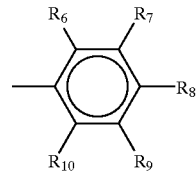

wherein $R_6$, $R_7$, $R_8$, $R_9$ and $R_{10}$ each independently, are —H or $C_1$–$C_{12}$ linear or branched or cyclic alkyl chain, aryl group, —$OR_{11}$, -alcohoxyhydroxy, hydroxyalkylthio-, —$SR_{11}$, —$S=OR_{12}$, —$SO_2R_{13}$, —$C=OR_{14}$, —$NR_{15}R_{16}$, CN, -halogen;, $R_{11}$ is —H, $C_1$–$C_{12}$ linear or branched alkyl chain, aryl group, $R_{12}$ is $C_1$–$C_{12}$ linear or branched alkyl chain, aryl group, $R_{13}$ is $C_1$–$C_{12}$ linear or branched alkyl chain, aryl group, —OH, —OAlkyl, —$NH_2$, —NHAlkyl, —N(Alkyl)$_2$, —NH Aryl, —N(Aryl)$_2$, $R_{14}$ is —H, $C_1$–$C_{12}$ linear or branched alkyl chain, aryl group, —OH, —OAlkyl, —$NH_2$, —NHAlkyl, —N(Alkyl)$_2$, —NH Aryl, —N(Aryl)$_2$, $R_{15}$ and $R_{16}$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, $R_4$ and $R_5$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, $X_2$ is a group

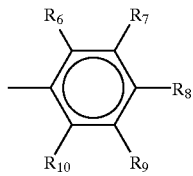

wherein $R_6$, $R_7$, $R_8$, $R_9$, $R_{10}$ have the meaning already stated or $X_2$ is a group

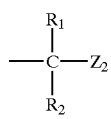

wherein $R_1$, $R_2$ have the meaning already stated, and $Z_2$ has the same meaning of $Z_1$ provided that $X_2$ is different from $X_1$ Y is: single bond, $C_1$–$C_{12}$ linear or branched alkylene, —O—, —S—, >S=O, >$SO_2$, —$NR_{17}$—, wherein $R_{17}$ is —H, $C_1$–$C_{12}$ linear or branched alkyl chain, aryl group, CO $R_1$.

The present invention further relates to photopolymerisable formulations containing at least one of the components of formula (I).

DETAILED DESCRIPTION OF THE INVENTION

Preferred photonitiators for pigmented systems are compounds of formula (I) in which:

Y is: single bond, —S—, —$NR_{17}$—, wherein $R_{17}$ is —H, $C_1$–$C_{12}$ linear or branched alkyl chain, aryl group, CO $R_1$.

Particularly preferred as photoinitiators for pigmented systems are compounds of formula (I) in which:

$X_1$ is a group

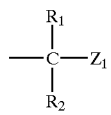

wherein $R_1$ and $R_2$, each independently, are —H or $C_1$–$C_{12}$ linear or branched or cyclic alkyl chain, aryl, alkylaryl groups.

$Z_1$ is —$SO_2R_3$, —$NR_4R_5$, halogen $R_3$ is: $C_1$–$C_{12}$ linear or branched alkyl chain, or:

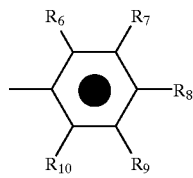

wherein $R_6$, $R_7$, $R_8$, $R_9$ and $R_{10}$ each independently, are —H or $C_1$–$C_{12}$ linear or branched or cyclic alkyl chain;

$R_4$ and $R_5$ are each independently, H, $C_1$–$C_{12}$ linear or branched alkyl, aryl, $COR_1$ or, if coincident, represent $C_2$–$C_6$ alkylene, $C_2$–$C_6$ oxa-, thia- or aza-alkylene, $X_2$ is a group

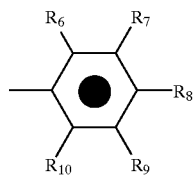

wherein $R_6$, $R_7$, $R_8$, $R_9$ and $R_{10}$ each independently, are —H or $C_1$–$C_{12}$ linear or branched or cyclic alkyl chain, aryl group,—$OR_{11}$, -alcohoxyhydroxy, hydroxyalkylthio-, —$SR_{11}$, —S=$OR_{12}$, —$SO_2R_{13}$, —C=$OR_{14}$, —$NR_{15}R_{16}$, CN, -halogen;

$R_{11}$ is —H, $C_1$–$C_{12}$ linear or branched alkyl chain, aryl group, $R_{12}$ is $C_1$–$C_{12}$ linear or branched alkyl chain, aryl group, $R_{13}$ is $C_1$–$C_{12}$ linear or branched alkyl chain, aryl group, —OH, —OAlkyl, —$NH_2$, —NHAlkyl, —N(Alkyl)$_2$, —NH Aryl, —N(Aryl)$_2$, $R_{14}$ is —H, $C_1$–$C_{12}$ linear or branched alkyl chain, aryl group, —OH, —OAlkyl, —$NH_2$, —NHAlkyl, —N(Alkyl)$_2$, —NH Aryl, —N(Aryl)$_2$, $R_{15}$ and $R_{16}$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, or a group

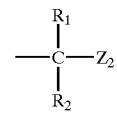

wherein $R_1$ and $R_2$, are defined above.

$Z_2$ is —$SO_2R_3$, —$NR_4R_5$, —$OR_1$, halogen wherein $R_1$, $R_3$, $R_4$ and $R_5$, are defined above Y is: —S—, —$NR_7$—, wherein $R_{17}$ is —H, $C_1$–$C_{12}$ linear or branched alkyl chain, aryl group, CO $R_1$.

Examples of compounds suitable for the application according to the present invention are the following, however the present invention is by no means limited thereto:

4-benzoyl-4'-(2-bromo-2-methyl-1-propanoyl) diphenylsulfide (1)

4-(4-methylbenzoyl)-4'-(2-bromo-2-methyl-1-propanoyl) diphenylsulfide (2)

4-(4-phenylbenzoyl)-4'-(2-bromo-2-methyl-1-propanoyl) diphenylsulfide (3)
4-(4-fluorobenzoyl)-4'-(2-bromo-2-methyl-1-propanoyl) diphenylsulfide (4)
4-(2-methylbenzoyl)-4'-(2-bromo-2-methyl-1-propanoyl) diphenylsulfide (5)
4-benzoyl-4'-(2-bromo-1-propanoyl)diphenylsulfide (6)
4-(2,4,6-trimethylbenzoyl)-4'-(2-bromo-2-methyl-1-propanoyl)diphenylsulfide (7)
4-(2-hydroxybenzoyl)-4'-(2-bromo-2-methyl-1-propanoyl) diphenylsulfide (8)
4-(4-methoxybenzoyl)-4'-(2-bromo-2-methyl-1-propanoyl) diphenylsulfide (9)
4-(4-cianobenzoyl)-4'-(2-bromo-2-methyl-1-propanoyl) diphenylsulfide (10)
4-benzoyl-4'-(2-bromo-2-phenyl-1-ethanoyl) diphenylsulfide (11)
4-benzoyl-4'-[2-(4-methylphenylsulfonyl)-2-methyl-1-propanoyl]diphenylsulfide (12)
4-(4-methylbenzoyl)-4'-[2-(4-methylphenylsulfonyl)-2-methyl-1-propanoyl]diphenylsulfide (13)
4-benzoyl-4'-phenylacetyl-diphenylsulfide (14)
4-benzoyl-4'-[2-(4-methylphenylsulfonyl)-2-phenyl-1-ethanoyl]diphenylsulfide (15)
4-(4-phenylbenzoyl)-4'-[2-(4-methylphenylsulfonyl)-2-methyl-1-propanoyl]diphenylsulfide (16)
4-(4-fluorobenzoyl)-4'-[2-(4-methylphenylsulfonyl)-2-methyl-1-propanoyl]diphenylsulfide (17)
4-(4-morpholinobenzoyl)-4'-[2-(4-methylphenylsulfonyl)-2-methyl-1-propanoyl]diphenylsulfide (18)
4-(2-methylbenzoyl)-4'-[2-(4-methylphenylsulfonyl)-2-methyl-1-propanoyl]diphenylsulfide (19)
4-benzoyl-4'-[2-(4-methylphenylsulfonyl)-1-propanoyl] diphenylsulfide (20)
4-(4-methoxybenzoyl)-4'-[2-(4-methylphenylsulfonyl)-2-methyl-1-propanoyl]diphenylsulfide (21)
4-(2,4,6-trimethylbenzoyl)-4'-[2-(4-methylphenylsulfonyl)-2-methyl-1-propanoyl]diphenylsulfide (22)
4-(2-hydroxybenzoyl)-4'-[2-(4-methylphenylsulfonyl)-2-methyl-1-propanoyl]diphenylsulfide (23)
4-(4-cianobenzoyl)-4'-[2-(4-methylphenylsulfonyl)-2-methyl-1-propanoyl]diphenylsulfide (24)
4-(4-mercaptobenzoyl )-4'-[2-(4-methylphenylsulfonyl)-2-methyl-1-propanoyl]diphenylsulfide (25)
4-benzoyl-4'-(2-methyl-2-morpholino-1-propanoyl) diphenylsulfide (26)
4-(2-methyl-2-morpholino-1propanoyl)-4'-(2-hydroxy-2-methyl-1-propanoyl) diphenylsulfide (27)
4-(2-methyl-2-hydroxy-1-propanoyl)-4'-[2-(4-methylphenylsulfonyl)-2-methyl-1-propanoyl] diphenylsulfide (28)
4-[4-(2-hydroxy-1-ethoxy)-benzoyl-]4'-[2-(4-methylphenylsulfonyl)-2-methyl-1-propanoyl] diphenylsulfide (29)
4-(2-methyl-2-morpholino-1-propanoyl)-4'-[2-(4-methylphenylsulfonyl)-2-methyl-1-propanoyl] diphenylsulfide (30)
4-[4-(2-hydroxyethylthio)-benzoyl-]4'-[2-(4-methylphenylsulfonyl)-2-methyl-1-propanoyl] diphenylsulfide (31)

According to the present invention, pigmented photopolymerisable formulations contain at least one of the following compounds: compound (12), compound (13), compound (15), compound (16), compound (17), compound (18), compound,(19), compound (20), compound (21), compound (22), compound (23), compound (24), compound (25), compound (26), compound (27), compound (28), compound (29), compound (30), compound (31).

According to the present invention, compounds having formula (I) are used as photoinitiators in photopolymerisable systems containing reactive monomers and oligomers. The words "photopolymerisable system" or "photopolymerisable formulation" means in the present text a mixture of photopolymerisable or cross-linkable monomers and oligomers, at least one photoinitiator, fillers pigments, dispersants, and other additives of general use. The expression "photopolymerisation" is meant in broad sense and includes, for instance, further polymerisation or cross-linking of polymeric material, for instance of prepolymers, homopolymerisation and copolymerisation of simple monomers, and combination of these reactions. Suitable monomers which can be used in the system described in the present invention, comprise: acrylonitrile, acrylamide and their derivatives; vinyl ethers; N-vinylpyrrolidone; mono and polyfunctional allyl ethers, such as trimethylolpropan-diallyl ether; styrenes and alpha-methylstyrenes; esters of acrylic and methacrylic acid with aliphatic alcohols, glycols, polyhydroxylated compounds, such as pentaerythritol or trimethylolpropane or amminoalcohols; esters of vinyl alcohol with aliphatic or acrylic acids; derivatives of fumaric and maleic acids.

Reactive oligomers, suitable for the present invention, include polyesters, polyacrylates, polyurethanes, epoxy resins, polyethers containing acrylic, fumaric or maleic functionalities. Pigments used comprise inorganic pigments such as titanium dioxide and "Carbon black", organic pigments based on azo, phtalocyanine, antraquinone etc.

Compounds of formula (I) of the present invention act as photoinitiators and may be used alone or in combination with other photoinitiators such as benzophenone, benzyldimethylketale, alpha-hydroxyketones, benzoin ethers, alpha-amminoketones etc. Particularly advantageous turns out the combination with tertiary amines, which increase the cross-linking rate and reduce oxygen inhibiting effects such as triethylamine, N-methyldiethanolamine, N,N-dimethylethanolamine, esters of p-dimethylaminobenzoic acid. For pigmented systems turns out particularly advantageous the use of sensitising substances or co-initiators, such as thioxanthones and their derivatives.

In addition to the compounds having formula (I), many components may be included in the photopolymerisable system, such as thermal stabilisers, sensitisers, photo-oxidation stabilisers such as sterically hindered amines, antioxidants, atmospheric oxygen exclusion agents, thermal generators of radicals such as organic and inorganic peroxides, peresters, hydroperoxydes, benzopinacols, azo-derivatives such as azoisobutyronitrile, metallic compounds such as cobalt (II) salts, manganese, antifoam, fillers, dyes, glass and carbon fibres, thixotropic agents. Other components are constituted by not-photopolymerisable polymers, present as chemically inert substances, such as nitrocellulose, polyacrylic esters, polyolefines, etc., or cross-linkable polymers by alternative routes such as peroxides and atmospheric oxygen or by acid catalysis or thermal activation, such as polyisocyanates, urea, melamine or epoxy resins. Such photopolymerisable systems may be either of transparent or pigmented kind, and they are used in printing, graphic arts, plastic materials, metals, wood, glass etc. fields. It is noteworthy their use in the inks field, above all those having high pigmentation level: in this application pigments are present in amounts ranging from 10 to 60% by weight, and preferably between 15 and 40%.

Compounds having formula (I) are generally used in a quantity of from 0.01% to 20% by weight, preferably from 0.5% to 5% by weight, based on the composition. They show great dispersability in photopolymerisable systems, to which they give high photochemical reactivity and light stability.

Examples of light sources used for photopolymerisation are high, medium or low-pressure mercury-vapour lamps, superactinic lamps or excimer lamps, with emission bands in the UV-vis region up to 400 nm. Among possible light sources even sunlight or other artificial sources, such as xenon, tungsten lamps, and laser sources are included. In cross-linking of inks containing titanium dioxide, "doped" lamps with a particularly high emission between 350 and 450 nm are preferably used.

In preparation of inks, the above mentioned compositions containing pigments are ground up to the obtainment of a granulometry comprised between 0.1 and 2 μm and preferably lower than 1 μm in a three cylinders refiner. Such grinding may be carried out either before or after the addition of a photoinitiator and co-initiator mixture, wherein the photoinitiator is contained in an amount of from 30% to 70% by weight. Finally the polymerisation is obtained by known methods, by irradiation at the suitable wavelength range.

The preparation of the above mentioned photoinitiators, having formula (I), can be performed by several methods described in scientific and patent literature and well known to those skilled in the art.

In particular compounds having formula (I), in which $Z_1$=—$SO_2R_3$ or halogen and $R_3$ has the above meaning already, $X_2$=

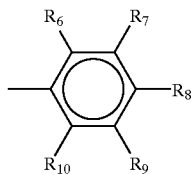

wherein $R_6$, $R_7$, $R_8$, $R_9$, $R_{10}$ have the above meaning, are preferably prepared according the following process comprising the following steps:

a) reacting an arylacylchloride of formula (II)

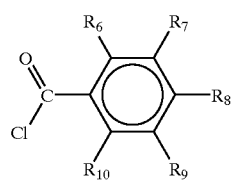

(II)

wherein $R_6$, $R_7$, $R_8$, $R_9$, $R_{10}$ have the meaning above defined with the exclusion of one of them being=—$NR_{15}R_{16}$, with the compound of formula (III)

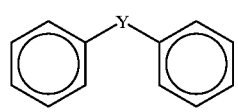

(III)

wherein Y has the above mentioned meaning in the presence of a Lewis acid such as, for instance, $AlCl_3$, at temperature comprised between 5° C. and 25° C., thereby obtaining the compound (IV)

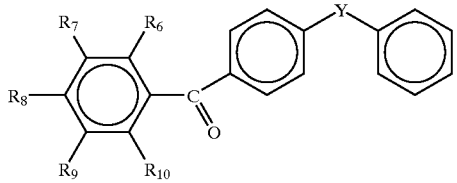

(IV)

b) reacting the intermediate (IV) with a dialkylhaloacetyl halogenide of formula (V):

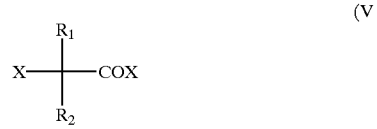

(V)

wherein $R_1$ and $R_2$ have the above meaning, except for $R_1$ or $R_2$=H and $R_1$ or $R_2$=Aryl; X=halogen, preferably Cl or Br, in the presence of a Lewis acid such as, for instance, $AlCl_3$, at temperature ranging from 5° C. and 25° C., to obtain compound (IA)

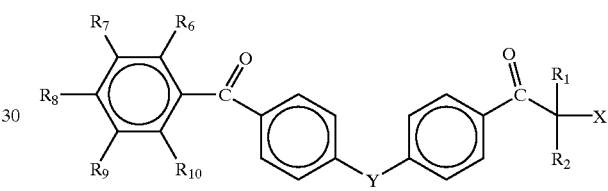

or b1) reacting intermediate (IV) with a dialkylacetyl halogenide of formula (VI):

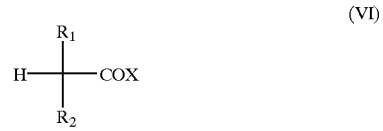

(VI)

wherein $R_1$ or $R_2$=H and $R_2$ or $R_1$=Aryl and X=halogen in the presence of a Lewis acid such as, for instance, $AlCl_3$, at temperature comprised between 5° C. and 25° C., thereby obtaining the intermediate of formula (VII)

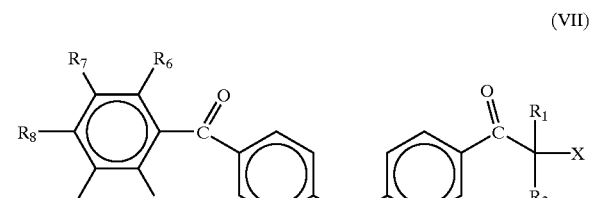

(VII)

which is further halogenated, preferably brominated or chlorinated thereby obtaining intermediate (IA) wherein $R_1$ or $R_2$=H and $R_2$ or $R_1$=Aryl and X=halogen.

c) reacting the intermediate of formula (IA) coming from step (b) or (b1), with the sodium sulfinate derivative of formula $R_3SO_2^-Na^+$, wherein $R_3$ has the significance already stated, in an organic solvent, preferably an alcohol or an amide, at a temperature of between 60° C.

and 120° C. thereby obtaining the compound of formula (IB)

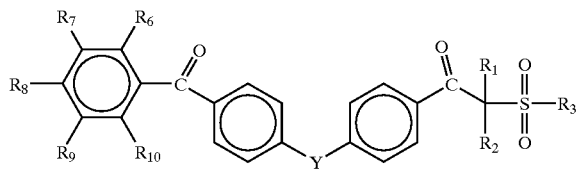

(IB)

d) optionally reacting derivative (IB) wherein $R_8$=halogen, with an amine of formula $NHR_{15}R_{16}$ thereby obtaining compound of formula (IC)

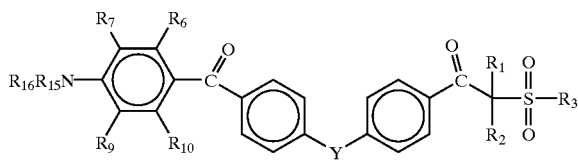

(IC)

Alternatively in the above-mentioned process, steps (a) and (b) can be carried out at the same time.

In particular the preferred process to synthesise compounds of formula (I) wherein $X_2$ is a group

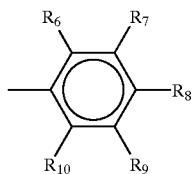

wherein $R_6$, $R_7$, $R_8$, $R_9$, $R_{10}$ have the above meaning and $X_1$ is a group

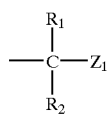

wherein $Z_1$ is $NR_4R_5$, besides steps (a), (b) or (b1) above mentioned, includes the following steps:

c') reacting the compound of formula (IA) obtained from (b) or (b1) with sodium methylate in methanol under reflux to obtain the intermediate of formula (VIII):

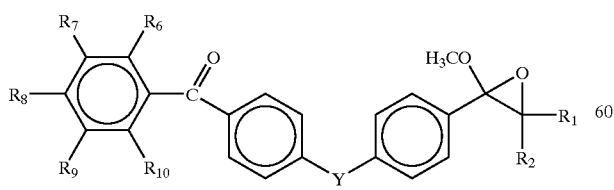

(VIII)

d') The intermediate of formula (VIII) reacts with the amine of formula $HNR_4R_5$ in anhydrous acetonitrile to obtain the compound of formula (I).

We report the following examples for illustrative but not limitative purposes of the preparation of the compounds of the present invention and of the photopolymerisable formulations.

EXAMPLE 1

4-benzoyl-4'-(2-bromo-2-methyl-1-propanoyl) diphenylsulfide (1)

To a solution of diphenylsulfide (9.3 g, 50 mmol) and of benzoyl chloride (7 g, 51 mmol) in 38 ml of $CH_2Cl_2$, $AlCl_3$ (6.8 g, 51 mmol) is added in small aliquots in 1 h, maintaining the temperature between 20 and 25° C. After stirring for 20 min, a solution of a-bromoisobutyrylbromide (11.7 g, 51 mmol) in 7.5 ml of $CH_2Cl_2$ is added dropwise. The reaction mixture is cooled to 10° C. and $AlCl_3$ (7 g, 52.5 mmol) is added in small aliquots in 1 h. After the addition, the reaction mixture is stirred for 1 h at 15–20° C., diluted with water under vigorous stirring and the pH is adjusted at 7–8 using sodium bicarbonate. The organic phase is washed twice with water, dried on $Na_2SO_4$ and the solvent is distilled. 22.2 g of a pink solid is obtained that is crystallised from EtOH 95% to give 18 g of a white crystalline product having a melting point of 111–112° C. $^1$HNMR (300 MHz, $CDCl_3$) 8.13 (m, 2H), 7.79 (m, 4H), 7.60 (m, 1H), 7.48 (m,4H), 7.39 (m, 2H), 2.30 (s, 6H).

EXAMPLE 2

4-benzoyl-4'-[2-(4-methylphenylsulfonyl)-2-methyl-1-propanoyl]diphenylsulfide (12)

A solution of 4-benzoyl-4'-(2-bromo-2-methyl-1-propanoyl)diphenylsulfide (8.8 g, 20 mmol) and of sodium p-toluensulfinate (4.5 g, 25 mmol) in 49 ml of n-BuOH is refluxed for 2.5 h. The reaction mixture is cooled to 90° and diluted with water (16 ml) to obtain phase separation. The organic layer is refluxed and after cooling 8.1 g of white solid are obtained (melting point 112–114° C.). $^1$HNMR (300 MHz, $CDCl_3$) 7.98 (m, 2H), 7.79 (m, 4H), 7.62 (m, 3H), 7.48 (m, 4H), 7.41 (m, 2H), 7.32 (m, 2H), 2.45 (s, 3H), 1.70 (s, 6H).

EXAMPLE 3

4-(4-methylbenzoyl)-4'-(2-bromo-2-methyl-1-propanoyl)diphenylsulfide (2)

According to the method described in example 1, 23.4 g of crude product (2) are obtained from 9.3 g (50 mmol) of diphenylsulfide and 8 g (51 mmol) of p-toluoyl chloride. After crystallisation with i-PrOH, 19 g of a white solid having melting point of 140° C. are obtained. $^1$HNMR (300 MHz, $CDCl_3$) 8.13 (m, 2H), 7.75 (m, 4H), 7.50 (m, 2H), 7.38 (m, 2H), 7.31 (m, 2H), 2.44 (s, 3H), 2.04 (s, 6H).

EXAMPLE 4

4-(4-methylbenzoyl)-4'-[2-(4-methylphenylsulfonyl)-2-methyl-1-propanoyl] diphenylsulfide (13)

According to the method described in example 2, 16.2 g of white solid having melting point of 130° C. (crystallisation from i-PrOH) are obtained starting from 7.8 g (41 mmol) of 4-(4-methylbenzoyl)-4'-(2-bromo-2-methyl-1-propanoyl)diphenylsulfide. $^1$HNMR (300 MHz, $CDCl_3$) 7.95 (m, 2H), 7.72 (m, 4H), 7.62 (m, 2H), 7.45 (m, 2H), 7.37 (m, 2H), 7.28 (m, 4H), 2.44 (s, 6H), 1.70 (s, 6H).

EXAMPLE 5

4-benzoyl-4-phenylacetyl-diphenylsulfide (14)

According to the method described in example 1, 20.8 g of a yellow solid are obtained from 9.3 g (50 mmol) of diphenylsulfide, 7.4 g (52 mmol) of benzoyl chloride and 8.2 g (52 mmol) of phenylacetylchloride. After crystallisation with n-PrOH, 18 g of a white solid having melting point of 144° C. are obtained. $^1$HNMR (300 MHz, CDCl$_3$) 7.92 (m, 2H), 7.74 (m, 4H), 7.54 (m, 1H), 7.39 (m, 6H), 7.23 (m, 5H), 4.23 (s, 2H).

EXAMPLE 6

4-benzoyl-4'-(2-bromo-2-phenyl-1-ethanoyl)diphenylsulfide (11)

To a solution of 4-benzoyl-4'-phenylacetyl-diphenylsulfide (17.1 g, 42 mmol) in 180 ml of CH$_2$Cl$_2$, 7 g (43.8 mmol) of bromine are added dropwise. After 10 min the reaction mixture is cooled and is diluted with a solution of Na$_2$SO$_3$, under vigorous stirring. After phase separation, the organic layer is dried on (Na$_2$SO$_4$) and the solvent is distilled. The solid residue is crystallised from n-PrOH to give 17.5 g of a product having melting point of 135° C. $^1$HNMR (300 MHz, CDCl$_3$) 7.91 (m, 2H), 7.77 (m, 4H), 7.58 (m, 1H), 7.48 (m, 6H), 7.33 (m, 5H), 6.32 (s, 1H).

EXAMPLE 7

4-benzoyl-4'-[2-(4-methylphenylsulfonyl)-2-phenyl-1-ethanoyl]diphenylsulfide (15)

According to the method described in example 2, 16.2 g of white solid having melting point of 167° C. are obtained starting from 16.7 g (34 mmol) of 4-benzoyl-4'-(2-bromo-2-phenyl-1-ethanoyl)diphenylsulfide. $^1$HNMR (300 MHz, CDCl$_3$) 7.79 (m, 6H), 7.59 (m, 1H), 7.47 (m, 6H), 7.30 (m, 7H), 7.19 (m, 2H), 6.07 (s, 1H), 2.42 (s, 3H).

EXAMPLE 8

4-(4-phenylbenzoyl)-4'-(2-bromo-2-methyl-1-propanoyl)diphenylsulfide (3)

According to the method described in example 1, 11 g of raw product are obtained from 3.82 g (20 mmol) of diphenylsulfide and 4.6 g (20.6 mmol) of 4-diphenylcarbonylchloride in 60 ml of CH$_2$Cl$_2$. After crystallisation from n-BuOH, a white solid having melting point of 144° C. is obtained. $^1$HNMR (300 MHz, CDCl$_3$) 8.14 (m, 2H), 7.89 (m, 2H), 7.81 (m, 2H), 7.71 (m, 2H), 7.64 (m, 2H), 7.48 (m, 4H), 7.41 (m, 3H), 2.05 (s, 6H).

EXAMPLE 9

4-(4-phenylbenzoyl)-4'-[2-(4-methylphenylsulfonyl)-2-methyl-1-propanoyl]diphenylsulfide (16)

According to the method described in example 2, a white solid having melting point of 98° C. (crystallisation from i-PrOH) are obtained starting from 3 g (5.8 mmol) of 4-(4-phenylbenzoyl)-4'-(2-bromo-2-methyl-1-propanoyl)diphenylsulfide.

$^1$HNMR (300 MHz, CDCl$_3$) 7.98 (m, 2H), 7.89 (m, 2H), 7.82 (m, 2H), 7.71 (m, 2H), 7.65 (m, 4H), 7.47 (m, 4H), 7.42 (m, 3H), 7.32 (m, 2H), 2.45 (s, 3H), 1.70 (s, 6H).

EXAMPLE 10

4-(4-fluorobenzoyl)-4'-(2-bromo-2-methyl-1-propanoyl)diphenylsulfide (4)

According to the method described in example 1, 23.8 g of raw product are obtained from 9.3 g (50 mmol) of diphenylsulfide and 8.33 g (51 mmol) of 4-fluorobenzoylchloride. After crystallisation with i-PrOH, 20 g of white solid having melting point of 140° C. are obtained. $^1$HNMR (300 MHz, CDCl$_3$) 8.14 (m, 2H), 7.84 (m, 2H), 7.75 (m, 2H), 7.47 (m, 2H), 7.40 (m, 2H), 7.17 (m, 2H), 2.05 (s, 6H).

EXAMPLE 11

4-(4-fluorobenzoyl)-4'-[2-(4-methylphenylsulfonyl)-2-methyl-1-propanoyl]diphenylsulfide (17)

According to the method described in example 2, 6.5 g of white solid having melting point of 144° C. (crystallisation from i-PrOH) are obtained starting from 7.1 g (15 mmol) of 4-(4-fluorobenzoyl)-4'-(2-bromo-2-methyl-1-propanoyl)diphenylsulfide. $^1$HNMR (300 MHz, CDCl$_3$) 7.99 (m, 2H), 7.85 (m, 2H), 7.75 (m, 2H), 7.65 (m, 2H), 7.44 (m, 4H), 7.32 (m, 2H), 7.18 (m, 2H), 2.46 (s, 3H), 1.70 (s, 6H).

EXAMPLE 12

4-(4-morpholinobenzoyl)-4'-[2-(4-methylphenylsulfonyl)-2-methyl-1-propanoyl]diphenylsulfide (18)

A solution of 4-(4-fluorobenzoyl)-4'-[2-(4-methylphenylsulfonyl)-2-methyl-1-propanoyl]diphenylsulfide (4.5 g, 8.4 mmol) in 40 ml of morpholine is refluxed for 9 h. The reaction mixture is cooled, diluted with water/ice, brought to pH 5–6 and extracted with CH$_2$Cl$_2$. After phase separation, the organic layer is dried on (Na$_2$SO$_4$) and the solvent is distilled. The glassy residue (5.4 g) is crystallised from n-PrOH to give 4.7 g of a product having melting point of 67–68° C. $^1$HNMR (300 MHz, CDCl$_3$) 8.00 (m, 2H), 7.82 (m, 2H), 7.75 (m, 2H), 7.68 (m, 2H), 7.52 (m, 2H), 7.38 (m, 4H), 6.93 (m, 2H), 3.89 (m, 4H), 3.36 (m, 4H), 2.45 (s, 3H), 1.72 (s, 6H).

EXAMPLE 13

4-(2-methylbenzoyl)-4'-(2-bromo-2-methyl-1-propanoyl)diphenylsulfide (5)

According to the method described in example 1, 13 g of a clear oil are obtained from 5.7 g (30 mmol) of diphenylsulfide and 4.8 g (31 mmol) of o-toluoyl chloride. $^1$HNMR (300 MHz, CDCl$_3$) 8.13 (m, 2H), 7.76 (m, 2H), 7.41 (m, 5H), 7.28 (m, 3H), 2.33 (s, 3H), 2.03 (s, 6H).

EXAMPLE 14

4-(2-methylbenzoyl)-4'-[2-(4-methylphenylsulfonyl)-2-methyl-1-propanoyl]diphenylsulfide (19)

According to the method described in example 2, 8 g of white solid having melting point of 72° C. are obtained starting from 11 g (24 mmol) of 4-(2-methylbenzoyl)-4'-(2-bromo-2-methyl-1-propanoyl)diphenylsulfide. $^1$HNMR (300 MHz, CDCl$_3$) 7.98 (m, 2H), 7.76 (m, 2H), 7.65 (m, 2H), 7.41 (m, 5H), 7.29 (m, 5H), 2.45 (s, 3H), 2.34 (s, 3H), 1.70 (s, 6H).

EXAMPLE 15

4-benzoyl-4'-(2-bromo-1-propanoyl)diphenylsulfide (6)

According to the method described in example 1, 22.2 g of a yellow oil are obtained from 9.3 g (50 mmol) of diphenylsulfide and 11.6 g (52 mmol) of 2-bromopropanoylbromide. After crystallisation with i-PrOH, a white solid having melting point of 105–106° C. is obtained. $^1$HNMR (300 MHz, CDCl$_3$) 7.98 (m, 2H), 7.80 (m, 4H), 7.61 (m, 1H), 7.50 (m, 4H), 7.41 (m, 2H), 5.25 (q, J=6.3 Hz 1H), 1.93 (d, J=6.3 Hz 3H).

EXAMPLE 16

4-benzoyl-4'-[2-(4-methylphenylsulfonyl)-1-propanoyl]diphenylsulfide (20)

According to the method described in example 2, 9 g of white solid having melting point of 140° C. are obtained starting from 8.5 g (20 mmol) of 4-benzoyl-4'-(2-bromo-1-propanoyl)diphenylsulfide. $^1$HNMR (300 MHz, CDCl$_3$) 7.94 (m, 2H), 7.81 (m, 4H), 7.63 (m, 3H), 7.52 (m, 4H), 7.39 (m, 2H), 7.33 (m, 2H), 5.1 (q, J=6.3 Hz 1H), 2.46 (s, 3H), 1.55 (d, J=6.3 Hz 3H).

EXAMPLE 17

4-(4-methoxybenzoyl)-4'-(2-bromo-2-methyl-1-propanoyl)diphenylsulfide (9)

According to the method described in example 1, 25 g of raw product are obtained from 9.3 g (50 mmol) of diphenylsulfide and 9 g (52 mmol) of 4-anisoyl chloride. After crystallisation with i-PrOH, 18.5 g of white solid having melting point of 134° C. are obtained. $^1$HNMR (300 MHz, CDCl$_3$) 8.10 (m, 2H), 7.81 (m, 2H), 7.73 (m, 2H), 7.47 (m, 2H), 7.36 (m, 2H), 6.95 (m, 2H), 3.88 (s, 3H), 2.03 (s, 6H).

EXAMPLE 18

4-(4-methoxybenzoyl)-4'-[2-(4-methylphenylsulfonyl)-2-methyl-1-propanoyl]diphenylsulfide (21)

According to the method described in example 2, 8.4 g of white solid having melting point of 160° C. are obtained starting from 9.4 g (20 mmol) of 4-(4-methoxybenzoyl)-4'-(2-bromo-2-methyl-1-propanoyl)diphenylsulfide. $^1$HNMR (300 MHz, CDCl$_3$) 7.98 (m, 2H), 7.83 (m, 2H), 7.75 (m, 2H), 7.65 (m, 2H), 7.49 (m, 2H), 7.39 (m, 2H), 7.32 (m, 2H), 6.98. (m, 2H), 3.90 (s, 3H), 2.45 (s, 3H), 1.70 (s, 6H).

EXAMPLE 19

A) Synthesis of 4-(2,4,6-trimethylbenzoyl) diphenylsulfide

To a solution of diphenylsulfide (9.3 g, 50 mmol) and of 2,4,6-trimethylbenzoyl chloride (10 g, 55 mmol) in 53 ml of CH$_2$Cl$_2$ AlCl$_3$ (6.9 g, 52 mmol) is added in small aliquots in 1 h, maintaining the temperature at 20° C. After stirring for 1 h, the reaction mixture is diluted with water and treated as reported in example 1. 7.5 g of a white solid having melting point of 72–73° C. are obtained. $^1$HNMR(300 MHz, CDCl$_3$) 7.65 (m, 2H), 7.52 (m, 2H), 7.40 (m, 3H), 7.14 (m, 2H), 6.86 (s, 2H), 2.33 (s, 3H), 2.06 (s, 6H).

B) Synthesis of 4-(2,4,6-trimethylbenzoyl)-4-(2-bromo-2-methyl-1-propanoyl)diphenylsulfide (7)

To a solution of 4-(2,4,6-trimethylbenzoyl) diphenylsulfide (7.2 g, 21 mmol) and of a-bromo isobutyryl bromide (5.2 g, 23 mmol) in 38 ml of CH$_2$Cl$_2$, AlCl$_3$ (9 g, 66 mmol) is added in small aliquots, maintaining the temperature at 20° C. After stirring for 1 h, the reaction mixture is diluted with water and treated as reported in example 1. 10.6 g of a clear oil are obtained. $^1$HNMR(300 MHz, CDCl$_3$) 8.13 (m, 2H), 7.73 (m, 2H), 7.42 (m, 2H), 7.36 (m, 2H), 6.88 (s, 2H), 2.32 (s, 3H), 2.08 (s, 6H), 2.03 (s, 6H).

EXAMPLE 20

4-(2,4,6-trimethylbenzoyl)-4'-[2-(4-methylphenylsulfonyl)-2-methyl-1-propanoyl] diphenylsulfide (22)

According to the method described in example 2, 5.5 g of white solid having melting point of 67–68° C. are obtained starting from 10.5 g (21.8 mmol) of 4-(2,4,6-trimethylbenzoyl)-4'-(2-bromo-2-methyl-1-propanoyl) diphenylsulfide. $^1$HNMR(300 MHz, CDCl$_3$) 7.92 (m, 2H), 7.69 (m, 2H), 7.59 (m, 2H), 7.37 (m, 2H), 7.29 (m, 4H), 6.84 (s, 2H), 2.39 (s, 3H), 2.27 (s, 3H), 2.04 (s, 6H), 1.63 (s, 6H).

EXAMPLE 21

A) Synthesis of 4-(2-methoxybenzoyl) diphenylsulfide

According to the method described in example 19, 5.3g of a solid having melting point of 84° C. are obtained from 6 g (31.5 mmol) of diphenylsulfide and 5.87 g (33.3 mmol) of o-anisoyl chloride in 56 ml of CH$_2$Cl$_2$ and crystallisation with n-hexane. $^1$HNMR(300 MHz, CDCl$_3$) 7.70 (m, 2H), 7.52 (m, 2H), 7.40 (m, 4H), 7.33 (m, 1H), 7.18 (m, 2H), 7.03 (m, 2H), 3.73 (s, 3H).

B) Synthesis of 4-(2-hydroxybenzoyl)-4'-(2-bromo-2-methyl-1-propanoyl)diphenylsulfide (8)

According to the method described in example 19, 5.9 g of an oil are obtained from 4.35 g (13.6 mmol) of 4-(2-methoxybenzoyl)diphenylsulfide and 4.4 g (19.1 mmol) of a-bromo isobutyryl bromide in 45 ml of CH$_2$Cl$_2$. $^1$HNMR (300 MHz, CDCl$_3$) 12.00 (s, 1H), 8.19 (m, 2H), 7.71 (m, 2H), 7.62 (m, 1H), 7.55 (m, 3H), 7.45 (m, 2H), 7.10 (m, 1H), 6.94 (m, 1H), 2.08 (s, 6H).

EXAMPLE 22

4-(2-hydroxybenzoyl)-4'-[2-(4-methylphenylsulfonyl)-2-methyl-1-propanoyl] diphenylsulfide (23)

According to the method described in example 2, 2.1 g of white solid having melting point of 146° C. are obtained starting from 2.7 g (5.9 mmol) of 4-(2-hydroxybenzoyl)-4'-(2-bromo-2-methyl-1-propanoyl)diphenylsulfide. $^1$HNMR (300 MHz, CDCl$_3$) 11.95 (s, 1H), 8.01 (m, 2H), 7.68 (m, 4H), 7.62 (m, 1H), 7.54 (m, 3H), 7.44 (m, 2H), 7.35 (m, 2H), 7.10 (m, 1H), 6.92 (m, 1H), 2.46 (s, 3H), 1.72 (s, 6H).

EXAMPLE 23

A) Synthesis of 4-(4-cianobenzoyl)diphenylsulfide

According to the method described in example 19, 6.9 g of a solid having melting point of 142–143° C. are obtained from 3.72 g (20 mmol) of diphenylsulfide and 3.81 g (22.5 mmol) of 4-cianobenzoyl chloride in 113 ml of $CH_2Cl_2$ and crystallisation with acetonitrile. $^1$HNMR (300 MHz, $CDCl_3$) 7.83 (m, 2H), 7.77 (m, 2H), 7.66 (m, 2H), 7.54 (m, 2H), 7.44 (m, 3H), 7.22 (m, 2H).

B) Synthesis of 4-(4-cianobenzoyl)-4'-(2-bromo-2-methyl-1-propanoyl)diphenylsulfide (10)

According to the method described in example 19, 3.6 g of a solid having melting point of 132–133° C. are obtained from 3 g (9.5 mmol) of 4-(4-cianobenzoyl)diphenylsulfide in 52 ml of $CH_2Cl_2$ by reaction at 0° C. and crystallisation with acetonitrile. $^1$HNMR (300 MHz, $CDCl_3$) 8.16 (m, 2H), 7.88 (m, 2H), 7.81 (m, 2H), 7.76 (m, 2H), 7.45 (m, 4H), 2.05 (s, 6H).

EXAMPLE 24

4-(4-cianobenzoyl)-4'-[2-(4-methylphenylsulfonyl)-2-methyl-1-propanoyl]diphenylsulfide (24)

According to the method described in example 2, 3.5 g of a raw product are obtained starting from 3.2 g (6.9 mmol) of 4-(4-cianobenzoyl)-4'-(2-bromo-2-methyl-1-propanoyl)diphenylsulfide. After crystallisation from i-PrOH 2 g of a product having melting point of 126–127° C. are obtained. $^1$HNMR (300 MHz, $CDCl_3$) 8.02 (m, 2H), 7.87 (m, 2H), 7.81 (m, 2H), 7.75 (m, 2H), 7.67 (m, 2H), 7.48 (m, 4H), 7.35 (m, 2H), 2.46 (s, 3H), 1.70 (s, 6H).

EXAMPLE 25

A) Synthesis of 1-[4-(4-benzoylthioanisyl)-phenyl]-1-methoxy-2-methyl-1,2-epoxypropane Into a refluxing solution of 4-benzoyl-4'-(2-bromo-2-methyl-1-propanoyl)diphenylsulfide (5 g, 11.39 mmol) in 300 ml of MeOH, a solution of 0.92 g (17.09 mmol) of MeONa in 20 ml of MeOH is added dropwise. After 5 min the reaction mixture is cooled and MeOH is evaporated. The white residue is treated with ethyl ether, filtered and the solid is washed with ethyl ether. The solution is evaporated to dryness and the raw product is crystallised from petroleum ether to obtain 4 g of a white product. $^1$HNMR (300 MHz, Acetone $d_6$) 7.82 (m, 4H), 7.72 (m, 1H), 7.63 (m, 6H), 7.45 (m, 2H), 3.23 (s, 3H), 1.55 (s, 3H), 1.06 (s, 3H).

B) Synthesis of 4-benzoyl-4'-(2-methyl-2-morpholino-1-propanoyl)diphenylsulfide (26)

Into a solution of 1-[4-(4-benzoylthioanisyl)-phenyl-1-methoxy-2-methyl-1,2-epoxy-propane (2.82 g, 7.23 mmol) and morpholine (6.3 g, 72.3 mmol) in 17 ml of anhydrous acetonitrile, 3.85 g (36.15 mmol) of anhydrous $LiClO_4$ and 6.38 g (72.3 mmol) of morpholine are added. The suspension is heated to 60° C. and reacted under stirring in argon atmosphere for 6 h. The reaction mixture is cooled, diluted with water (150 ml) and extracted with ethyl ether. The organic layer is dried on $Na_2SO_4$, filtered and evaporated to dryness. After crystallisation with MeOH, 2.6 g of white solid having melting point of 119° C. are obtained. $^1$HNMR (300 MHz, $CDCl_3$) 8.55 (m, 2H), 7.80 (m, 4H), 7.63 (m, 1H), 7.50 (m, 4H), 7.38 (m, 2H), 3.70 (m, 4H), 2.58 (m, 4H), 1.33 (s, 6H).

EXAMPLE 26

Synthesis of 4-(2-methyl-1-propanoyl)-4-(2-bromo-2-methyl-1-propanoyl)diphenylsulfide According to the method described in example 1, 39 g of a solid product having melting point of 79° C. are obtained from 37.1 g (199 mmol) of diphenylsulfide, 47.4 g (206 mmol) of a-bromoisobutyrylbromide and 22.5 g (215 mmol) of isobutyryl chloride and after two crystallisations respectively with acetonitrile and petroleum ether. $^1$HNMR (300 MHz, $CDCl_3$) 8.12 (d,2H), 7.92 (d,2H), 7.45 (d, 2H), 7.37 (d,2H), 3.52 (m,1H), 2.04 (s,6H), 1.23 (d,6H).

B) Synthesis of 4-(2-morpholino-2-methylpropanoyl)-4'-(2-methylpropanoyl) diphenylsulfide According to the method described in example 25 A, 14.4 g of yellow oil are obtained from 4-(2-methyl-1-propanoyl)-4'-(2-bromo-2-methyl-1-propanoyl)diphenylsulfide (15.5 g, 38 mmol).

The yellow liquid (14.4 g) is reacted according to the method described in example 25 B, to obtain 9.4 g of yellow oil. $^1$HNMR (300 MHz, $CDCl_3$) 8.52 (d,2H), 7.92 (d,2H), 7.44 (d, 2H), 7.36 (d,2H), 3.68 (dd,4H), 3.52 (m,1H), 2.53 (dd,4 H),1.32 (s,6H), 1.22 (d,6H).

C) Synthesis of 4-(2-morpholino-2-methyl-1-propanoyl)-4'-(2-bromo-2-methyl-1-propanoyl) diphenylsulfide To a solution of 4-(2-morpholino-2-methyl-1-propanoyl)-4'-(2-methylpropanoyl)diphenylsulfide (9.4 g, 23 mmol) in 100 g of $CH_2BrCl$ and a catalytic amount of benzoyl peroxide, 3.8 g (24 mmol) of bromine are added dropwise. The reaction mixture is heated at 66° C. for 30 min, then it is washed with water. The organic layer is dried on $Na_2SO_4$ and the solvent is distilled. The oil residue is chromatographed on silica gel (eluent toluene/ethyl acetate 95/5) to obtain 3.8 g of dark red oil. $^1$HNMR (300 MHz, $CDCl_3$) 8.52 (d,2H), 8.17 (d,2H), 7.40 (d, 4H), 3.69 (m,4H), 2.57 (m,4H), 2.05 (s,6H), 1.32 (s,6H).

D) Synthesis of 4-(2-methyl-2-morpholino-1-propanoyl)-4'-(2-hydroxy-2-methyl-1propanoyl) diphenylsulfide (27)

A mixture of 4-(2-morpholino-2-methylpropanoyl)-4'-(2-bromo-2-methylpropanoyl)diphenylsulfide (3.2 g, 6.5 mmol), of a 20% aqueous solution of NaOH (1.7 g, 8.5 mmol) and of tetrabutylammonium bromide (0.1 g) in 3 g of $CH_2Cl_2$ is refluxed under stirring for 15 min. The reaction mixture is diluted with water and, after phase separation, the organic layer is dried on $Na_2SO_4$. The solvent is evaporated to dryness under vacuum to obtain 2.8 g of brown oil. $^1$HNMR (300 MHz, CDCl3) 8.52 (d,2H), 8.00 (d,2H), 7.40 (d, 4H), 3.67 (m,4H), 2.57 (m,4H), 1.62 (s,6H), 1.32 (s,6H).

EXAMPLE 27

A) Synthesis of 4,4'-bis(2-bromo-2-methyl-1-propanoyl)diphenylsulfide

To a solution of a-bromoisobutyryl bromide (40 g, 174 mmol) in 63 g of $CH_2BrCl$, 24 g (180 mmol) of $AlCl_3$ are added under stirring in $N_2$ atmosphere in small aliquots in 1 h, maintaining the temperature at 10° C. The temperature is raised up to 20–25° C., then a solution of diphenylsulfide (16 g, 86 mmol) in 6 g of $CH_2BrCl$ is added dropwise in 1 h. The reaction mixture is stirred 3 h at the same temperature. The reaction is quenched on ice/HCl 37% (1/1); after phase separation the aqueous layer is extracted two times with CH$_2$BrCl. The organic layers are washed with a saturated solution of Na$_2$CO$_3$, dried with anhydrous Na$_2$SO$_4$, and the organic solvent is evaporated to dryness under vacuum. The crude residue is crystallised from MeOH to obtain 67.4 g of product. $^1$HNMR (300 MHz, CDCl3) 8.13 (d, 4H), 7.41 (d, 4H), 2.06 (s, 12H).

B) Synthesis of 4-(2-methyl-2-hydroxy-1-propanoyl)-4'-[2-(4-methylphenylsulfonyl)-2-methyl-1-propanoyl]diphenylsulfide (28)

24 g (50 mmol) of 4,4'-bis(2-bromo-2-methyl-1-propanoyl)diphenylsulfide are reacted according to the method described in example 26 D, using n-butanol (75 g) as solvent. The reaction mixture is added with sodium p-toluensulfinate (25 g, 127 mmol) and refluxed for 1 h. The mixture is cooled, diluted with water and the organic layer is concentrated under vacuum. The product crystallises by cooling to give 22 g of a white-pink solid. A sample is purified by chromatography on silica gel (eluent toluene/ethyl acetate 8/2) to obtain 0.58 g of a glassy oil. $^1$HNMR (300 MHz, CDCl3) 7.98 (2d, 4H), 7.65 (d,2H), 7.42 (2d, 4H), 7.32 (d,2H), 2.46 (s,3H), 1.68 (s,6H), 1.63 (s,6H).

EXAMPLE 28

Synthesis of 4-(2-methyl-2-morpholino-1-propanoyl)-4'-[2-(4-methylphenylsulfonyl)-2-methyl-1-propanoyl]diphenylsulfide (30).

A solution of 4-(2-morpholino-2-methyl-1-propanoyl)-4'-(2-bromo-2-methyl-1-propanoyl)diphenylsulfide (3.1 g, 6.3 mmol) and of sodium p-toluensulfinate (1.35 g, 7.5 mmol) in DMF (10 g) is heated to 60° C. for 30 min. The reaction mixture is cooled and poured in water. The precipitate is collected by filtration to obtain 3.5 g of dry solid. $^1$HNMR (300 MHz, CDCl3) 8.54 (d,2H), 7.96 (d,2H), 7.65 (d, 2H), 7.36 (m,6H), 3.70 (m,4H), 2.58 (m,4H), 2.44 (s,3H), 1.68 (s,6H),1.32 (s,6H).

EXAMPLE 29

A) Synthesis of 4-[4-(2-hydroxy-ethylthio)-benzoyl-]-4'-(2-methyl-1-propanoyl)diphenylsulfide According to the method described in example 1, 6.46 g of a white solid product are obtained from 2.92 g (15.7 mmol) of diphenylsulfide, 3.09 g, (15.7 mmol) of p-bromobenzoyl chloride and 2.11 g (19.8 mmol) of isobutyryl chloride. 4.46 g of the white solid product are dissolved into 60 ml of DMF under stirring. To the solution, heated to 50° C. under nitrogen atmosphere, 0.78 ml (11.1 mmol) of 2-hydroxy ethanthiol and 0.45 g (11.2 mmol) of sodium hydride 60% in 44.6 ml of DMF are added dropwise. After 90 min a further addition of a solution of 0.17 ml (2.4 mmol) of 2-hydroxy ethanthiol and 0.1 g (2.5 mmol) of sodium hydride 60% in 10 ml of DMF is carried out. After 15 min the reaction mixture is poured in water and extracted with ethyl ether. The organic layer is washed with water, dried with Na$_2$SO$_4$ and the solvent is evaporated to dryness under vacuum. The crude product is chromatographed on silica gel (eluent: petroleum ether/ethyl acetate 7/3) to obtain 2.1 g of whitish solid. $^1$HNMR (300 MHz, CDCl3) 7.93 (d,2H), 7.74 (d,4H), 7.43 (m, 6H), 3.76 (t,2H), 3.51 (m,1H), 3.23 (t,2H), 1.22 (d,6H).

B) Synthesis of 4-[4-(2-hydroxy-ethylthio)-benzoyl-]-4'-(2-bromo-2-methyl-1-propanoyl) diphenylsulfide To a solution of 4-[4-(2-hydroxy-ethylthio)-benzoyl-]-4'-(2-methyl-1-propanoyl)diphenylsulfide (1.5 g, 3.4 mmol) in 20 g of CH$_2$Cl$_2$, 0.56 g (3.5 mmol) of bromine and a catalytic amount of benzoyl peroxide are added. The mixture is reacted for 16 h at room temperature then the solvent is evaporated to dryness under vacuum. The raw product is chromatographed on silica gel (eluent CH$_2$Cl$_2$/MeOH 98/2) to obtain 0.32 g of yellowish solid. $^1$HNMR (300 MHz, CDCl3) 8.12 (d,2H), 7.74 (d,4H), 7.46 (d, 2H), 7.35 (dd, 4H), 3.85 (t,2H), 3.24 (t,2H), 2.04 (s,6H).

C) Synthesis of 4-[4-(2-hydroxy-ethylthio)-benzoyl-]-4-[2-(4-methylphenylsulfonyl)-1-methyl-1-propanoyl]diphenylsulfide (31)

A solution of 4-[4-(2-hydroxy-ethylthio)-benzoyl-]-4'-(2-bromo-2-methyl-1-propanoyl)diphenylsulfide (0.32 g, 0.62 mmol) and of sodium p-toluensulfinate (0.13 g, 0.7 mmol) in n-BuOH (3.5 ml) is refluxed for 2.5 h then 0.13 g of sodium p-toluensulfinate are added and the mixture is further refluxed for 2 h. The reaction mixture is cooled, poured in water, extracted with CH$_2$Cl$_2$ and dried on Na$_2$SO$_4$. The solvent is distilled off and the raw product is chromatographed on silica gel (eluent CH$_2$Cl$_2$/MeOH 99/1) to obtain 0.17 g of white solid. $^1$HNMR (300 MHz, CDCl3) 7.91 (d, 2H), 7.75–7.52 (m, 6H), 7.42–7.22 (m, 8H), 3.78 (t, 2H), 3.15 (t, 2H), 2.39 (s, 3H), 1.62 (s, 6H).

The substances used in the following examples can be found on the market under commercial brand names: Ebecryl 600®, UCB (Belgium); Ebecryl 350®, UCB (Belgium); Ebecryl 220®, UCB (Belgium); Trimethylolpropanetriacrylate (TMPTA); Irgalite Blue BNSF®, CIBA; Verol 368®, Lamberti SpA; Esacure EDB®, Lamberti SpA.

In the next example the following compounds are used:

4-benzoyl-4'-[2-(4-methylphenylsulfonyl)-2-methyl-1-propanoyl]diphenylsulfide (12)
4-(2-methylbenzoyl)-4'-[2-(4-methylphenylsulfonyl)-2-methyl-1-propanoyl]diphenylsulfide (19)
4-(4-phenylbenzoyl)-4'-[2-(4-methylphenylsulfonyl)-2-methyl-1-propanoyl]diphenylsulfide (16)
4-(2,4,6-trimethylbenzoyl)-4'-[2-(4-methylphenylsulfonyl)-2-methyl-1-propanoyl]diphenylsulfide (22)
4-benzoyl-4'-[2-(4-methylphenylsulfonyl)-2-phenyl-1-ethanoyl]diphenylsulfide (15)
4-benzoyl-4'-[2-(4-methylphenylsulfonyl)-1-propanoyl]diphenylsulfide (20)
4-benzoyl-4'-(2-methyl-2-morpholino-1-propanoyl)diphenylsulfide (26)
4-(2-methyl-2-morpholino-1-propanoyl)-4'-(2-hydroxy-2-methyl-1-propanoyl)diphenylsulfide (27)
4-(2-methyl-2-hydroxy-1-propanoyl)-4'-[2-(4-methylphenylsulfonyl)-2-methyl-1-propanoyl]diphenylsulfide (28)
4-(2-methyl-2-morpholino-1-propanoyl)-4'-[2-(4-methylphenylsulfonyl)-2-methyl-1-propanoyl]diphenylsulfide (30).

EXAMPLE 30

Composition of the matrix for the blue ink (% w/w)

| | |
|---|---|
| Ebecryl 600 ® | 37.3% |
| Ebecryl 350 ® | 0.9% |
| Ebecryl 220 ® | 10.4% |
| TMPTA | 31.9% |
| Verol 368 ® | 1.5% |
| Irgalite Blue BNSF ® | 18.0% |

Ink preparations: the compositions of the formulations based on the matrix with addition of co-initiator and photoinitiator are reported in Table (I). The formulations are ground on a three cylinders refiner up to reaching a granulometry lower than one micron and photocross-linked by irradiation in the conditions reported below.

TABLE I

Composition (% w/w) of photocross-linkable blue inks

| | 1 | 2 | 3 | 4 | 5 | 6 | 7 | 8 | 9 | 10 |
|---|---|---|---|---|---|---|---|---|---|---|
| Matrix | 94 | 94 | 94 | 94 | 94 | 94 | 94 | 94 | 94 | 94 |
| Compound (12) | 3 | | | | | | | | | |
| Compound (19) | | 3 | | | | | | | | |
| Compound (16) | | | 3 | | | | | | | |
| Compound (22) | | | | 3 | | | | | | |
| Compound (15) | | | | | 3 | | | | | |
| Compound (20) | | | | | | 3 | | | | |
| Compound (26) | | | | | | | 3 | | | |
| Compound (27) | | | | | | | | 3 | | |
| Compound (28) | | | | | | | | | 3 | |
| Compound (30) | | | | | | | | | | 3 |
| Esacure EDB | 3 | 3 | 3 | 3 | 3 | 3 | 3 | 3 | 3 | 3 |

The evaluation of the obtained inks is carried out analysing the following parameters: reactivity and post curing odour.

Reactivity

The ink is applied with a thickness of 1 micron, by a mechanical coater IGT on a paper support; then it is passed under the light source at a distance of 11 cm. The apparatus for irradiation is a Steinmann® photocross-linker, equipped with a medium pressure mercury lamp of 80 W/cm. The photocross-linking rate is measured with the line rate, (m/min) at which a complete photopolymerisation occurs (tack-free). The photopolymerisation is complete when the ink does not show any superficial damage after repeated pressure and twists of the thumb on the surface (thumb twist test). The higher the line rate to obtain tack-free, the higher is the reactivity of the photoinitiator.

Post Curing Odour

The tested inks, photopolymerised as reported above to obtain complete polymerisation, are each immediately and hermetically closed in a container and each container is put into an oven set at 60° C. After 1 h, a group of 5 persons opens each container and gives a judgement on the residual odour of each tested ink. The evaluation is qualitative and it is expressed on an empirical scale from 1 to 5:1 means minimum odour, 5 means a strong odour. The evaluation is carried out in double blind conditions.

TABLE 2

Reactivity and post curing odour results

| Ink | 1 | 2 | 3 | 4 | 5 | 6 | 7 | 8 | 9 | 10 |
|---|---|---|---|---|---|---|---|---|---|---|
| Reactivity (line speed: m/min) | 21.0 | 21.5 | 24.5 | 20.0 | 21.0 | 22.0 | 26.0 | 17.5 | 20.5 | 13.5 |
| Odour (mean of 5 evaluations) | 1 | 1 | 1 | 1 | 1 | 1 | 1 | 1 | 1 | 1 |

From the above data, photoinitiators 12, 19, 16, 22, 15, 20, 26, 27, 28, 30 have a very good reactivity in the examined ink and they have the advantage to give a very low post curing odour.

In the next example the following compounds have been used:

4-benzoyl-4'-[2-(4-methylphenylsulfonyl)-2-methyl-1-propanoyl]diphenylsulfide (12) benzophenone (A)

4-(2-phenylsulphonyl-2-methyl-1-propanoyl) diphenylsulfide (described in EP 192967) (B)

4,4'-bis[2-(4-methylphenylsulphonyl)-2-methyl-1-propanoyl)diphenylsulfide (described in EP 850253) (C)

4,4'-bis-phenylthio benzophenone, obtained by acylation of diphenylsulfide by 4-phenylthiobenzoil chloride (D)

EXAMPLE 31

Composition of the Matrix for the Blue Ink (% w/w)

| | |
|---|---|
| Ebecryl 600 ® | 37.3% |
| Ebecryl 350 ® | 0.9% |
| Ebecryl 220 ® | 10.4% |
| TMPTA | 31.9% |
| Verol 368 ® | 1.5% |
| Irgalite Blue BNSF ® | 18.0% |

Each ink has been added with 3% of Esacure EDB and variable amounts of photoinitiators. The first ink has been prepared adding 3 g of compound (12) to 100 g of the matrix added with Esacure EDB. The other inks has been prepared adding amounts of compounds A, B, C and D calculated to obtain the same molar ratios as those of compound (12) reported in Table 3. In this way each ink contains the same number of active functional groups (suitable to generate radicals). In the same table the total amount of photoinitiators (in g/100 g of matrix Son added with Esacure EDB) is reported.

TABLE 3

Ink composition

| Photoinitiator | Ink 1 | 2 | 3 | 4 |
|---|---|---|---|---|
| Compound (12) | 1 | | | |
| Compound (A) | | 1 | | 1 |
| Compound (B) | | 1 | | |
| Compound (C) | | | ½ | ½ |
| Compound (D) | | | 1 | |
| * | 3 | 3.37 | 4.17 | 2.91 |

* = g of photoinitiator/100 g of total matrix
Ink preparations as well as their reactivity evaluations has been done as reported in example 30 except for the layer thickness which was 3 microns.

TABLE 4

| Ink | 1 | 2 | 3 | 4 |
|---|---|---|---|---|
| | Results | | | |
| Line speed (m/min) | 30 | 11 | 19 | 10 |

From the results reported in table 4, photoinitiator (12) has a significantly higher reactivity than those of mixtures of photoinitiators containing equivalent amounts of reactive groups. This behaviour supports a synergistic effect when two active functional groups are in the same molecule.

What is claimed is:

1. Compounds useful as photoinitiators for photopolymerization, having formula (I)

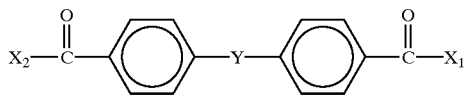

(I)

wherein $X_1$ and $X_2$ are different, $X_1$ is a group

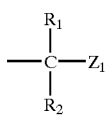

wherein $R_1$ and $R_2$, each independently, are —H or $C_1$–$C_{12}$ linear or branched or cyclic alkyl chain, aryl, alkylaryl groups, $Z_1$ is —$SO_2R_3$, —$NR_4R_5$ —$OR_1$, halogen, $R_3$ is: $C_1$–$C_{12}$ linear or branched alkyl chain, or:

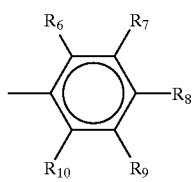

wherein $R_5$, $R_7$, $R_8$, $R_9$ and $R_{10}$ each independently, are —H, $C_1$–$C_{12}$ linear or branched or cyclic alkyl chain, aryl group —$OR_{11}$, hydroxyalkyloxy-, hydroxyalkylthio-, —$SR_{11}$, —S=$OR_{12}$, —$SO_2R_{13}$, —C=$OR_{14}$, —$NR_{15}R_{16}$, —CN, -halogen;

$R_{11}$, is —H, $C_1$–$C_{12}$ linear or branched alkyl chain, aryl group, $R_{12}$ is $C_1$–$C_{12}$ linear or branched alkyl chain, aryl group, $R_{13}$ is $C_1$–$C_{12}$ linear or branched alkyl chain, aryl group, —OH, —OAlkyl, —$NH_2$ —NHAlkyl, —N(Alkyl)$_2$—NHAryl, —N(Aryl)$_2$, $R_{14}$ is —H, $C_1$–$C_{12}$ linear or branched alkyl chain, aryl group, —OH, —OAlkyl, —$NH_2$, —NHAlkyl, —N(Alkyl)$_2$, —NHAryl, —N(Aryl)$_2$, $R_{15}$ and $R_{16}$, each independently, are —H, $C_1$–$C_{12}$ linear or branched alkyl chain, aryl group, $COR_1$, or, if coincident, represent $C_2$–$C_6$ oxa-, thia- or aza-alkylene, $R_4$ and $R_5$, each independently, are —H, $C_1$–$C_{12}$ linear or branched alkyl chain, aryl group, $COR_1$ or, $R_4$ and $R_5$ together represent $C_2$–$C_6$ alkylene, $C_2$–$C_6$ oxa-, thia- or aza-alkylene, $X_2$ is a group

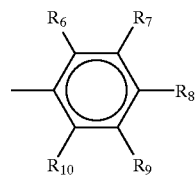

wherein $R_6$, $R_7$, $R_8$, $R_9$, $R_{10}$ have the above-mentioned meanings or a group

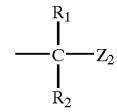

wherein $R_1$, $R_2$ have the above mentioned meanings, and $Z_2$ has the same meaning as $Z_1$ provided that $X_2$ is different from $X_1$, Y is: —O, —S—, >S=O, >$SO_2$, —$NR_{17}$— wherein $R_{17}$ is —H, $C_1$–$C_{12}$ linear or branched alkyl chain, aryl group or $COR_1$.

2. Compounds according to claim 1, wherein $X_1$ is a group

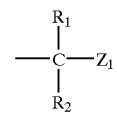

wherein $R_1$ and $R_2$, each independently, are —H or $C_1$–$C_{12}$ linear or branched or cyclic alkyl chain, aryl, alkylaryl groups.

$Z_1$ is —$SO_2R_3$, —$NR_4R_5$, halogen $R_3$ is: $C_1$–$C_{12}$ linear or branched alkyl chain, or:

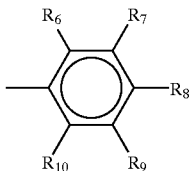

wherein $R_6$, $R_7$, $R_8$, $R_9$ and $R_{10}$ each independently, are —H or $C_1$–$C_{12}$ linear or branched or cyclic alkyl chain;

$R_4$ and $R_5$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, $X_2$ is a group

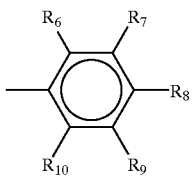

wherein $R_6$, $R_7$, $R_8$, $R_9$ and $R_{10}$ each independently, are —H or $C_1$–$C_{12}$ linear or branched or cyclic alkyl chain, aryl group, —$OR_{11}$, hydroxyalkyloxy-, hydroxyalkylthio-, —$SR_{11}$, —$S=OR_{12}$, —$SO_2R_{13}$, —$C=OR_{14}$, —$NR_{15}R_{16}$, —CN, -halogen;

$R_{11}$, is —H, $C_1$–$C_{12}$ linear or branched alkyl chain, aryl group, $R_{12}$ is $C_1$–$C_{12}$ linear or branched alkyl chain, aryl group, $R_{13}$ is $C_1$–$C_{12}$ linear or branched alkyl chain, aryl group, —OH, —OALkyl, —$NH_2$, —NHAlkyl, —N(Alkyl)$_2$, —NHAryl, —N(Aryl)$_2$, $R_{14}$ is —H, $C_1$–$C_{12}$ linear or branched alkyl chain, aryl group, —OH, —OAlkyl, —$NH_2$, —NHAlkyl, —N(Alkyl)$_2$, —NHAryl, —N(Aryl)$_2$, $R_{15}$ and $R_{16}$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, or a group

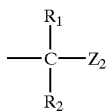

wherein $R_1$ and $R_2$, have the above mentioned meanings, $Z_2$ is —$SO_2R_3$, —$NR_4R_5$, —$OR_1$, halogen wherein $R_1$, $R_3$, $R_4$ and $R_5$, are defined above, Y is: —S—, —$NR_{17}$—, wherein $R_{17}$ is —H, $C_1$–$C_{12}$ linear or branched alkyl chain, aryl group and $COR_1$.

3. A compound according to claim 1, selected from the group consisting of:

4-benzoyl-4'-[2-(4-methylphenylsulfonyl)-2-methyl-1-propanoyl]diphenylsulfide, 4-(4-methylbenzoyl)-4'-[2-(4-methylphenylsulfonyl)-2-methyl-1-propanoyl]diphenylsulfide, 4-benzoyl-4'-[2-(4-methylphenylsulfonyl)-2-phenyl-1-ethanoyl]diphenylsulfide, 4-(4-morpholinobenzoyl)-4'-[2-(4-methylphenylsulfonyl)-2-methyl-1-propanoyl]diphenylsulfide, 4-(2-methylbenzoyl)-4'-[2-(4-methylphenylsulfonyl)-2-methyl-1-propanoyl]diphenylsulfide, 4-benzoyl-4'-[2-(4-methylphenylsulfonyl)-1-propanoyl]diphenylsulfide, 4-(4-methoxybenzoyl)-4'-[2-(4-methylphenylsulfonyl)-2-methyl-1-propanoyl]diphenylsulfide, 4-(2,4,6-trimethylbenzoyl)-4'-[2-(4-methylphenylsulfonyl)-2-methyl-1-propanoyl]diphenylsulfide, 4-(2-hydroxybenzoyl)-4'-[2-(4-methylphenylsulfonyl)-2-methyl-1-propanoyl]diphenylsulfide, 4-(4-cianobenzoyl)-4'-[2-(4-methylphenylsulfonyl)-2-methyl-1-propanoyl]diphenylsulfide, 4-(4-mercaptobenzoyl)-4'-[2-(4-methylphenylsulfonyl)-2-methyl-1-propanoyl]diphenylsulfide, 4-benzoyl-4'-(2-methyl-2-morpholino-1-propanoyl)diphenylsulfide, 4-(2-methyl-2-morpholino-1-propanoyl)-4'-(2-methyl-2-hydroxy-1-propanoyl)diphenylsulfide, 4-(2-methyl-2-hydroxy-1-propanoyl)-4'-[2-(4-methylphenylsulfonyl)-2-methyl-1-propanoyl]diphenylsulfide, 4-[4-(2-hydroxy-1-ethoxy)-benzoyl]-4'-[2-(4-methylphenylsulfonyl)-2-methyl-1-propanoyl]diphenylsulfide, 4-(2-methyl-2-morpholino-1-propanoyl)-4'-[2-(4-methylphenylsulfonyl)-2-methyl-1-propanoyl]diphenylsulfide, and 4-(2-methyl-2-morpholino-1-propanoyl)-4'-[2-(4-methylphenylsulfonyl)-2-methyl-1-propanoyl]diphenylsulfide.

4. Compounds according to claim 1, wherein $X_1$ is a group

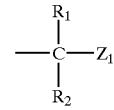

wherein $R_1$ and $R_2$, each independently, are —H or $C_1$–$C_{12}$ linear or branched or cyclic alkyl chain, aryl, alkylaryl groups, $Z_1$ is —$SO_2R_3$, —$NR_4R_5$, halogen $R_3$ is: $C_1$–$C_{12}$ linear or branched alkyl chain, or:

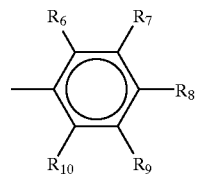

wherein $R_6$, $R_7$, $R_8$, $R_9$ and $R_{10}$ each independently, are —H or $C_1$–$C_{12}$ linear or branched or cyclic alkyl chain;

$R_4$ and $R_5$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, $X_2$ is a group

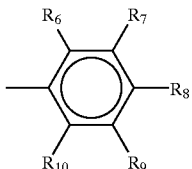

wherein $R_6$, $R_7$, $R_8$, $R_9$ and $R_{10}$ each independently, are —H or $C_1$–$C_{12}$ linear or branched or cyclic alkyl chain, aryl group, —$OR_{11}$, hydroxyalkyloxy-, hydroxyalkylthio-, —$SR_{11}$, —S=$OR_{12}$, —$SO_2R_{13}$, —C=$OR_{14}$, —$NR_{15}R_{16}$, —CN, -halogen;

$R_{11}$ is —H, $C_1$–$C_{12}$ linear or branched alkyl chain, aryl group, $R_{12}$ is $C_1$–$C_{12}$ linear or branched alkyl chain, aryl group, $R_{13}$ is $C_1$–$C_{12}$ linear or branched alkyl chain, aryl group, —OH, —OAlkyl, —$NH_2$, —NHAlkyl, —N(Alkyl)$_2$, —NHAryl, —N(Aryl)$_2$, $R_{14}$ is —H, $C_1$–$C_{12}$ linear or branched alkyl chain, aryl group, —OH, —OAlkyl, —$NH_2$, —NHAlkyl, —N(Alkyl)$_2$, —NHAryl, —N(Aryl)$_2$, $R_{15}$ and $R_{16}$, each independently, are —H, $C_1$–$C_{12}$ linear or branched alkyl chain, aryl group, $COR_1$ or, if coincident, represent $C_2$–$C_6$ alkylene, $C_2$–$C_6$ oxa-, thia- or aza-alkylene, or a group

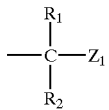

wherein $R_1$ and $R_2$, have the above mentioned meanings, $Z_2$ is —$SO_2R_3$, —$NR_4R_5$, —$OR_1$, halogen wherein $R_1$, $R_3$, $R_4$, and $R_5$, are defined above, Y is: —S—, —$NR_{17}$—, wherein $R_{17}$ is —H, $C_1$–$C_{12}$ linear or branched alkyl chain, aryl group and $COR_1$.

5. A compound according to claim 1, selected from the group consisting of:

4-benzoyl-4'-[2-(4-methylphenylsulfonyl)-2-methyl-1-propanoyl]diphenylsulfide, 4-(4-methylbenzoyl)-4'-[2-(4-methylphenylsulfonyl)-2-methyl-1-propanoyl]diphenylsulfide, 4-benzoyl-4'-[2-(4-methylphenylsulfonyl)-2-phenyl-1-ethanoyl]diphenylsulfide, 4-(4-phenylbenzoyl)-4'-[2-(4-methylphenylsulfonyl)-2-methyl-1-propanoyl]diphenylsulfide, 4-(4-fluorobenzoyl)-4'-[2-(4-methylphenylsulfonyl)-2-methyl-1-propanoyl]diphenylsulfide, 4-(4-morpholinobenzoyl)-4'-[2-(4-methylphenylsulfonyl)-2-methyl-1-propanoyl]diphenylsulfide, 4-(2-methylbenzoyl)-4'-[2-(4-methylphenylsulfonyl)-2-methyl-1-propanoyl]diphenylsulfide, 4-benzoyl-4'-[2-(4-methylphenylsulfonyl)-1-propanoyl]diphenylsulfide, 4-(4-methoxybenzoyl)-4'-[2-(4-methylphenylsulfonyl)-2-methyl-1-propanoyl]diphenylsulfide, 4-(2,4,6-trimethylbenzoyl)-4'-[2-(4-methylphenylsulfonyl)-2-methyl-1-propanoyl]diphenylsulfide, 4-(2-hydroxybenzoyl)-4'-[2-(4-methylphenylsulfonyl)-2-methyl-1-propanoyl]diphenylsulfide, 4-(4-cianobenzoyl)-4'-[2-(4-methylphenylsulfonyl)-2-methyl-1-propanoyl]diphenylsulfide, 4-(4-mercaptobenzoyl)-4'-[2-(4-methylphenylsulfonyl)-2-methyl-1-propanoyl]diphenylsulfide, 4-benzoyl-4'-(2-methyl-2-morpholino-1-propanoyl)diphenylsulfide, 4-(2-methyl-2-morpholino-1-propanoyl)-4'-(2-methyl-2-hydroxy-1-propanoyl)diphenylsulfide, 4-(2-methyl-2-hydroxy-1-propanoyl)-4'-[2-(4-methylphenylsulfonyl)-2-methyl-1-propanoyl]diphenylsulfide 4-[4-(2-hydroxy-1-ethoxy)-benzoyl]-4'-[2-(4-methylphenylsulfonyl)-2-methyl-1-propanoyl]diphenylsulfide, 4-(2-methyl-2-morpholino-1-propanoyl)-4'-[2-(4-methylphenylsulfonyl)-2-methyl-1-propanoyl]diphenylsulfide, and 4-[4-(2-hydroxyethylthio)-benzoyl]-4'-[2-(4-methylphenylsulfonyl)-2-methyl-1-propanoyl]diphensylsulfide.

6. A compound according to claim 2, selected from the group consisting of:

4-benzoyl-4'-[2-(4-methylphenylsulfonyl)-2-methyl-1-propanoyl]diphenylsulfide, 4-(4-methylbenzoyl)-4'-[2-(4-methylphenylsulfonyl)-2-methyl-1-propanoyl]diphenylsulfide, 4-benzoyl-4'-[2-(4-methylphenylsulfonyl)-2-phenyl-1-ethanoyl]diphenylsulfide, 4-(4-phenylbenzoyl)-4'-[2-(4-methylphenylsulfonyl)-2-methyl-1-propanoyl]diphenylsulfide, 4-(4-fluorobenzoyl)-4'-[2-(4-methylphenylsulfonyl)-2-methyl-1-propanoyl]diphenylsulfide, 4-(4-morpholinobenzoyl)-4'-[2-(4-metylphenylsulfonyl)-2-methyl-1-propanoyl]diphenylsulfide, 4-(2-methylbenzoyl)-4'-[2-(4-methylphenylsulfonyl)-2-methyl-1-propanoyl]diphenylsulfide, 4-benzoyl-4'-[2-(4-methylphenylsulfonyl)-1-propanoyl]diphenylsulfide, 4-(4-methoxybenzoyl)-4'-[2-(4-methylphenylsulfonyl)-2-methyl-1-propanoyl]diphenylsulfide, 4-(2,4,6-trimethylbenzoyl)-4'-[2-(4-methylphenylsulfonyl)-2-methyl-1-propanoyl]diphenylsulfide, 4-(2-hydroxybenzoyl)-4'-[2-(4-methylphenylsulfonyl)-2-methyl-1-propanoyl]diphenylsulfide, 4-(4-cianobenzoyl)-4'-[2-(4-methylphenylsulfonyl)-2-methyl-1-propanoyl]diphenylsulfide, 4-(4-mercaptobenzoyl)-4'-[2-(4-methylphenylsulfonyl)-2-methyl-1-propanoyl]diphenylsulfide, 4-benzoyl-4'-(2-methyl-2-morpholino-1-propanoyl)diphenylsulfide, 4-(2-methyl-2-morpholino-1-propanoyl)-4'-(2-methyl-2-hydroxy-1-propanoyl)diphenylsulfide, 4-(2-methyl-2-hydroxy-1-propanoyl)-4'-[2-(4-methylphenylsulfonyl)-2-methyl-1-propanoyl]diphenylsulfide, 4-[4-(2-hydroxy-1-ethoxy)-benzoyl]-4'-[2-(4-methylphenylsulfonyl)-2-methyl-1-propanoyl]diphenylsulfide, 4-(2-methyl-2-morpholino-1-propanoyl)-4'-[2-(4-methylphenylsulfonyl)-2-methyl-1-propanoyl]diphenylsulfide and 4-[4-(2-hydroxyethylthio)-benzoyl]-4'-[2-(4-methylphenylsulfonyl)-2-methyl-1-propanoyl]diphenylsulfide.

* * * * *